United States Patent [19]

Koenig et al.

[11] 4,257,974

[45] Mar. 24, 1981

[54] PROCESS FOR THE PREPARATION OF α,β-DIHALOALKYL ISOCYANATES

[75] Inventors: Karl-Heinz Koenig, Frankenthal; Heinz-Guenter Oeser; Karl-Heinz Feuerherd, both of Ludwigshafen, all of Fed. Rep. of Germany

[73] Assignee: BASF Aktiengesellscahft, Fed. Rep. of Germany

[21] Appl. No.: 85,962

[22] Filed: Oct. 18, 1979

[30] Foreign Application Priority Data

Oct. 24, 1978 [DE] Fed. Rep. of Germany ....... 2846184

[51] Int. Cl.³ .............. C07C 119/042; C07C 119/045; C07C 119/048
[52] U.S. Cl. ......................... 260/453 A; 260/453 AP; 260/453 AL; 260/453 AR
[58] Field of Search ..... 260/453 A, 453 AL, 453 AR

[56] References Cited

U.S. PATENT DOCUMENTS

| | | | |
|---|---|---|---|
| 3,468,923 | 9/1969 | Koenig et al. | 260/453 AL |
| 3,472,886 | 10/1969 | Harper et al. | 260/453 AL X |
| 3,535,360 | 10/1970 | Holtschmidt et al. | 260/453 AL |
| 3,862,201 | 1/1975 | Koenig et al. | 260/453 P |

FOREIGN PATENT DOCUMENTS 1122058 1/1962 Fed. Rep. of Germany .

*Primary Examiner*—Dolph H. Torrence
*Attorney, Agent, or Firm*—Keil & Witherspoon

[57] ABSTRACT

α,β-Dihaloalkyl isocyanates and a process for the preparation of such compounds by reacting α,β-unsaturated alkyl isocyanates with halogen in the presence of an organic solvent which is inert under the reaction conditions, at from −35° to +90° C. The α,β-dihaloalkyl isocyanates thus obtainable correspond to the formula

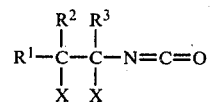

where $R^1$, $R^2$ and $R^3$ are identical or different and each is hydrogen, a saturated aliphatic radical of 1 to 10 carbon atoms, a cycloaliphatic radical of 3 to 12 carbon atoms, an araliphatic radical of 7 to 11 carbon atoms or an aromatic radical of 6 to 10 carbon atoms, or $R^1$ and $R^2$ together with the carbon atom on which they are present as substituents are cycloalkyl of 3 to 7 ring members, and X is halogen. The compounds are valuable intermediates for the preparation of dyes, surface-coating intermediates, crop protection agents and drugs.

1 Claim, No Drawings

PROCESS FOR THE PREPARATION OF α,β-DIHALOALKYL ISOCYANATES

The present invention relates to α,β-dihaloalkyl isocyanates and to a process for the preparation of such compounds by reacting halogens with α,β-unsaturated alkyl isocyanates.

α,β-Dihaloalkyl isocyanates were not previously known, with the exception of α,β-dichloroethyl isocyanate. The latter is obtained on carrying out a substituting chlorination of β-chloroethyl isocyanate with elementary chlorine, which additionally results in substantial amounts of β,β-dichloroethyl isocyanate and of trichloroethyl, tetrachloroethyl and pentachloroethyl isocyanate isomers (German Pat. No. 1,122,058).

We have found that an α,β-dihaloalkyl isocyanate of the general formula I

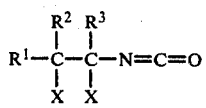

where $R^1$, $R^2$ and $R^3$ are identical or different and each is hydrogen, a saturated aliphatic radical of 1 to 10 carbon atoms, a cycloaliphatic radical of 3 to 12 carbon atoms, an araliphatic radical of 7 to 11 carbon atoms or an aromatic radical of 6 to 10 carbon atoms, or $R^1$ and $R^2$ together with the carbon atom on which they are present as substituents are cycloalkyl of 3 to 7 ring members, and X is halogen, is obtained in a particularly advantageous manner if an α,β-unsaturated alkyl isocyanate of the formula II

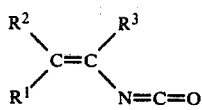

where $R^1$, $R^2$ and $R^3$ have the above meanings, is reacted with a halogen of the formula $X_2$ at from $-35°$ to $+90°$ C. in the presence of an organic solvent which is inert under the reaction conditions.

This previously unknown method of synthesis, ie. the reaction of elementary halogen with α,β-unsaturated alkyl isocyanates, gives α,β-dihaloalkyl isocyanates in good yield and high purity by a simple and economical method. The smooth course of the reaction was in no way foreseeable, since Angew. Chemie 74 (1962), 848–855 discloses that the hydrogen atoms of aliphatic isocyanates can be replaced by halogen even under very mild reaction conditions; however, halogenation by substitution releases hydrogen halide which, as in the case of vinyl isocyanate, readily leads to polymerization of the α,β-unsaturated isocyanate (German Pat. No. 1,173,454; Ann. Chem. 244 (1888), 35). In the process according to the invention, neither polymerization nor substitution, but only an addition reaction of elementary halogen, is observed.

The α,β-dihaloalkyl isocyanates of the formula I, where $R^1$, $R^2$ and $R^3$ may be identical or different and each is hydrogen, a saturated aliphatic radical of 1 to 10 carbon atoms, a cycloaliphatic radical of 3 to 12 carbon atoms, an araliphatic radical of 7 to 11 carbon atoms or an aromatic radical of 6 to 10 carbon atoms, or $R^1$ and $R^2$ together with the carbon atom on which they are present as substituents are cycloalkyl of 3 to 7 ring members, and X is halogen, with the proviso that $R^1$, $R^2$ and $R^3$ are not all simultaneously hydrogen if X is chlorine, are novel.

The α,β-dihaloalkyl isocyanates obtainable according to the invention are valuable intermediates for the synthesis of, for example, dyes, surface-coating intermediates, crop protection agents and drugs, since they contain three reactive centers of different chemical reactivity, namely the isocyanate group, the very reactive α-halogen atom and the less reactive β-halogen atom. Their further reactions present no difficulties, since the compounds, in contrast to the α-haloisocyanates known from the literature, are not also present as the isomeric alkylidene-carbamyl halides. These latter compounds very easily hydrolyze because of their C=N double bond, ie. their usefulness as starting materials or intermediates is greatly restricted by their instability.

The process according to the invention may be used for the preparation of α,β-dihaloalkyl isocyanates of the formula I, where X is halogen, preferably chlorine or bromine, and the radicals $R^1$, $R^2$ and $R^3$ are hydrogen, a saturated aliphatic radical of 1 to 10 carbon atoms, for example unbranched or branched alkyl of 1 to 10 carbon atoms, which is unsubstituted or substituted by halogen or by alkoxy of 1 to 4 carbon atoms, a cycloaliphatic radical of 3 to 12 carbon atoms, for example monocycloalkyl of 3 to 8 carbon atoms or bicycloalkyl of 6 to 12 carbon atoms, an araliphatic radical of 7 to 11 carbon atoms, for example aralkyl of 7 to 11 carbon atoms, or an aromatic radical of 6 to 10 carbon atoms, which may be substituted by halogen, eg. fluorine, chlorine, bromine or iodine, by alkoxy of 1 to 4 carbon atoms or by nitro. $R^1$ and $R^2$, together with the carbon atom on which they are present as substituents, may also be cycloalkyl of 3 to 7 ring members.

Specific examples of $R^1$, $R^2$ and $R^3$ are: as alkyl, methyl, ethyl, n-propyl, isopropyl, n-butyl, sec.-butyl, isobutyl, n-pentyl, 3-methylbutyl, n-hexyl, 4-methylpentyl, 1-methylhexyl, n-heptyl, n-octyl, 3-methylheptyl, 4-methyloctyl, 2,2-dimethylhexyl or n-decyl, each of which may be substituted by halogen, eg. fluorine, chlorine, bromine or iodine, or by alkoxy of 1 to 4 carbon atoms, eg. methoxy, ethoxy, n-propoxy, isopropoxy or one of the isomeric butoxy groups; as monocycloalkyl or bicycloalkyl, cyclopropyl, cyclopentyl, cyclohexyl, bicyclo[2.2.1]hept-2-yl, cyclooctyl, bicyclo[3.2.1]oct-3-yl, bicyclo[5.2.0]non-4-yl and bicyclo[4.3.2]undec-2-yl; as aralkyl, benzyl, phenethyl, 1-phenylethyl, and α- or β-menaphthyl; as aromatic radicals, phenyl or naphthyl, each of which may be monosubstituted or polysubstituted by halogen, eg. fluorine, chlorine, bromine or iodine, by alkoxy of 1 to 4 carbon atoms, eg. methoxy, ethoxy, n-propoxy, isopropoxy, n-butoxy, sec.-butoxy or isobutoxy, or by nitro.

The process according to the invention is used preferentially to prepare α,β-dihaloalkyl isocyanates of the formula I, where $R^1$ is hydrogen or unbranched or branched alkyl of 1 to 6 carbon atoms and $R^2$ and $R^3$ are hydrogen or unbranched or branched alkyl of 1 to 4 carbon atoms, especially methyl, or $R^1$ and $R^2$ together with the carbon atom on which they are present as substituents are cycloalkyl of 5 or 6 ring members.

The addition reaction of a halogen with an α,β-unsaturated alkyl isocyanate takes place smoothly at from $-35°$ to $+90°$ C., preferably from $-10°$ to $+30°$ C. If the temperature range of from $-35°$ to $+90°$ C. is adhered to, it prevents the formation of product mixtures, for example through elimination of hydrogen halide from the α,β-dihaloalkyl isocyanate formed, giving a β-haloalkenyl isocyanate, from which, in turn, an α,β,β-trihaloalkyl isocyanate can result by addition reaction with halogen.

The reaction is carried out in the presence of an organic solvent which is inert under the reaction conditions. Suitable solvents are aliphatic chlorohydrocarbons, eg. methylene chloride, carbon tetrachloride, chloroform and 1,2-dichloroethane, and aromatic hydrocarbons, eg. benzene and toluene. Mixtures of these solvents may also be used.

The reaction may be carried out under atmospheric or superatmospheric pressure, preferably under a pressure of from 1 to 3 bars, batchwise or continuously.

Advantageously, the reaction is carried out with equimolar amounts of the α,β-unsaturated alkyl isocyanate of the formula II and the halogen of the formula $X_2$. However, it is also possible to employ either component in slight excess, preferably of up to 10 mole%.

To carry out the reaction, either the halogen or the α,β-unsaturated alkyl isocyanate may first be introduced into the inert organic solvent, after which the second reactant is added slowly whilst stirring and with control of temperature. After the addition, stirring is continued for from 1 to 20 hours. The solvent is then stripped off under reduced pressure and the residue is fractionally distilled, also under reduced pressure.

The α,β-dihaloalkyl isocyanates obtainable according to the invention can be purified by distillation under reduced pressure, with temperatures of from about 10° to 90° C. in the distillation vessel, without causing elimination of hydrogen halide.

The Examples which follow illustrate the process according to the invention.

EXAMPLE 1

315 parts by weight of chlorine gas are introduced into 4,500 parts by weight of dry methylene chloride at 0° C. 370 parts by weight of propen-1-yl isocyanate are added dropwise whilst stirring and maintaining the temperatue at −5° C. by cooling. The mixture is then stirred for 12 hours at room temperature, after which the solvent is stripped off under reduced pressure. 650 parts by weight of crude product, containing 80% of α,β-dichloro-n-propyl isocyanate, are obtained. The compound may be obtained pure by fractional distillation under reduced pressure.

Boiling point: 52°–56° C./27 mbar; $n_D^{20} = 1.4670$. calculated: C 31.2% H 3.3%; N 9.1%; Cl 46.0%; found: C 31.4% H 3.5%; N 9.3%; Cl 45.9%.

EXAMPLE 2

13.5 parts by weight of chlorine gas are introduced into 180 parts by weight of dry methylene chloride and 29 parts by weight of n-octen-1-yl isocyanate, whilst stirring and maintaining the temperature at from 0° to +15° C. by cooling. The mixture is then stirred for one hour at room temperature, after which the solvent is stripped off under reduced pressure. 42 parts by weight of crude product, containing 80% of α,β-dichloro-n-octyl isocyanate, are obtained. To obtain the pure product, a portion of the crude product is fractionally distilled under reduced pressure.

Boiling point: 75°–77° C./0.27 mbar; $n_D^{20} = 1.4652$. calculated: C 48.2%; H 6.8%; N 6.3%; Cl 31.6%; found: C 48.3%; H 6.6%; N 6.6%; Cl 31.3%.

EXAMPLE 3

Following the procedure described in Example 2, 150 parts by weight of vinyl isocyanate and 372 parts by weight of bromine at from 0° to +5° C. give 420 parts by weight of crude α,β-dibromoethyl isocyanate; purity: 96%.

Boiling point: 78°–79° C./24 mbar; $n_D^{20} = 1.5515$. calculated: C 15.7%; H 1.3%; N 6.1%; Br 69.8%; found: C 15.5%; H 1.4%; N 6.1%; Br 71.0%.

EXAMPLE 4

Following the procedure described in Example 1, 143 parts by weight of vinyl isocyanate and 145 parts by weight of chlorine at from −5° to −20° C. give 272 parts by weight of crude product, containing 85% of α,β-dichloroethyl isocyanate.

Boiling point: 50° C./32 mbar; $n_D^{20} = 1.4733$. calculated: C 25.7%; H 2.1%; N 10.0%; Cl 50.7%; found: C 26.0%; H 1.8%; N 9.7%; Cl 50.2%.

EXAMPLE 5

Following the procedure described in Example 1, 300 parts by weight of chlorine and 410 parts by weight of n-buten-1-yl isocyanate at from 0° to +5° C. give 700 parts by weight of crude product, containing 80% of α,β-dichloro-n-butyl isocyanate.

Boiling point: 75° C./33 mbar; $n_D^{20} = 1.4673$ calculated: C 35.7%; H 4.2%; O 9.5%; N 8.3%; Cl 42.2%; found: C 35.4%; H 4.2%; O 9.6%; N 8.5%; Cl 43.0%.

EXAMPLE 6

Following the procedure described in Example 2, 56.5 parts by weight of 2-methyl-buten-1-yl isocyanate and 36 parts by weight of chlorine at from 0° to +5° C. give 89 parts by weight of 96% pure α,β-dichloro-β-methyl-n-butyl isocyanate.

Boiling point: 84° C./27 mbar; $n_D^{20} = 1.4697$. calculated: N 7.7%; O 8.8%; Cl 38.9%; found: N 8.0%; O 8.8%; Cl 39.4%.

EXAMPLE 7

Following the procedure described in Example 1, 51 parts by weight of chlorine and 99.5 parts by weight of cyclohexylidene-methyl isocyanate at from 0° to +5° C. give 158 parts by weight of crude α-chloro-α-(1-chlorocyclohexyl)-methyl isocyanate. Purity: 82%.

Boiling point: 78° C./0.4 mbar; $n_D^{20} = 1.5037$. calculated: C 46.2%; H 5.3%; N 6.7%; Cl 34.1%; found: C 46.1%; H 5.2%; N 7.0%; Cl 34.7%.

We claim:

1. A process for the preparation of an α,β-dihaloalkyl isocyanate of the formula I

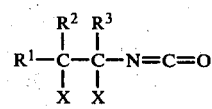

where $R^1$, $R^2$ and $R^3$ are identical or different and each is hydrogen, a saturated aliphatic radical of 1 to 10 carbon atoms, a cycloaliphatic radical of 3 to 12 carbon atoms, an araliphatic radical of 7 to 11 carbon atoms or an aromatic radical of 6 to 10 carbon atoms, or $R^1$ and $R^2$ together with the carbon atom on which they are present as substituents are cycloalkyl of 3 to 7 ring members, and X is halogen, wherein an α,β-unsaturated alkyl isocyanate of the formula II
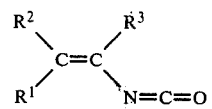
where $R^1$, $R^2$ and $R^3$ have the above meanings, is reacted with a halogen of the formula $X_2$ at from $-35°$ to $+90°$ C. in the presence of an organic solvent which is inert under the reaction conditions.
* * * * *